US008295503B2

(12) United States Patent
Sung et al.

(10) Patent No.: US 8,295,503 B2

(45) Date of Patent: Oct. 23, 2012

(54) NOISE REDUCTION DEVICE AND METHOD THEREOF

(75) Inventors: Po-Hsun Sung, Kaohsiung (TW); Chun-Hsun Chu, Tainan (TW)

(73) Assignee: Industrial Technology Research Institute, Hsinchu (TW)

( * ) Notice: Subject to any disclaimer, the term of this patent is extended or adjusted under 35 U.S.C. 154(b) by 1282 days.

(21) Appl. No.: 11/892,778

(22) Filed: Aug. 27, 2007

(65) Prior Publication Data

US 2008/0159554 A1 Jul. 3, 2008

(30) Foreign Application Priority Data

Dec. 29, 2006 (TW) ............................... 95149726 A

(51) Int. Cl.
*G10K 11/16* (2006.01)
*A61F 11/06* (2006.01)
*H04R 1/10* (2006.01)

(52) U.S. Cl. ..................... 381/71.5; 381/71.6; 381/71.1; 381/71.2; 381/71.8; 381/72; 381/74

(58) Field of Classification Search ................. 381/71.6, 381/71.5, 71.8, 72, 73.1, 317, 71.1, 71.2
See application file for complete search history.

(56) References Cited

U.S. PATENT DOCUMENTS 4,425,481 A * 1/1984 Mansgold et al. ............ 381/317
4,455,675 A 6/1984 Bose et al.
4,466,581 A 8/1984 Hill
4,829,571 A 5/1989 Kakiuchi et al.
4,833,719 A * 5/1989 Carme et al. .................... 381/72
4,852,683 A 8/1989 Killion
4,922,542 A 5/1990 Sapiejewski
4,985,925 A 1/1991 Langberg et al.
5,208,868 A 5/1993 Sapiejewski
5,457,749 A * 10/1995 Cain et al. .................... 381/71.5
5,497,427 A 3/1996 Nageno
5,668,883 A 9/1997 Abe et al.
5,740,258 A * 4/1998 Goodwin-Johansson ...... 381/72
5,832,094 A 11/1998 Le Her
5,852,667 A * 12/1998 Pan et al. ..................... 381/71.1
(Continued)

FOREIGN PATENT DOCUMENTS

CN 1688179 A 10/2005
(Continued)

*Primary Examiner* — Devona Faulk
*Assistant Examiner* — George Monikang
(74) *Attorney, Agent, or Firm* — Birch, Stewart, Kolasch & Birch, LLP

(57) ABSTRACT

A noise reduction device include at east a cavity; a plurality of ducts noise reduction, at least one of the ducts being connected to the cavity for transmitting an acoustic signal including a noise signal into/out of the cavity; a noise reduction circuit, for receiving the acoustic signal including the noise signal and generating an electrical signal; a microphone for receiving the acoustic signal inside the cavity, converting the received acoustic signal into another electrical signal and transmitting the electrical signal to the noise reduction circuit; and a speaker for receiving the electrical signal generated by the noise reduction circuit, using the received electrical signal to generate an out of phase acoustic signal accordingly, and feeding the out of phase acoustic signal into the cavity to interfere with the noise signal inside the cavity. With the noise reduction circuit and cavity structure designed in the noise reduction device, the full range of noise is attenuated.

20 Claims, 7 Drawing Sheets

U.S. PATENT DOCUMENTS

| | | | | |
|---|---|---|---|---|
| 6,597,792 | B1 | 7/2003 | Sapiejewski | |
| 6,683,965 | B1 | 1/2004 | Sapiejewski | |
| 6,801,629 | B2 | 10/2004 | Brimhall et al. | |
| 6,831,984 | B2 | 12/2004 | Sapiejewski | |
| 2003/0095670 | A1 * | 5/2003 | Wurtz | 381/71.6 |
| 2004/0240678 | A1 | 12/2004 | Nakamura et al. | |
| 2005/0226432 | A1 | 10/2005 | Lee | |
| 2005/0226439 | A1 | 10/2005 | Ludeman | |
| 2007/0253567 | A1 * | 11/2007 | Sapiejewski | 381/71.6 |

FOREIGN PATENT DOCUMENTS

| | | | |
|---|---|---|---|
| TW | 446258 | U | 7/2001 |
| TW | 091213715 | | 9/2002 |
| TW | 562382 | U | 11/2003 |
| TW | 595238 | B | 6/2004 |
| TW | I236857 | B | 7/2005 |

* cited by examiner

NOISE REDUCTION DEVICE AND METHOD THEREOF

FIELD OF THE INVENTION

The present invention relates to a noise reduction device and method. With noise reduction circuit and cavity structure designed in the noise reduction device, it can achieve reduction of audio high-frequency range noises by an operation of a low-pass filter formed by the cavity structure, and the reduction of audio low-frequency range noise by the noise reduction circuit as it also can direct a speaker to generate an out of phase acoustic wave for canceling out the audio low-frequency range noise, so that audio full frequency range noise reduction is achieved.

BACKGROUND OF THE INVENTION

Long exposure to noise can damage the eardrum of the inner ear, causing permanent hearing loss. Even only exposing to a loud noise for a short period of time might cause discomfort. Recent reports show that today's young people seem to be experiencing hearing loss at an astonishing rate, and that personal audio equipment seems to be contributing to that trend as like any other sound, music can cause hearing loss if it is loud enough and exposure is long enough. Especially when earbuds or earpieces are often used with such personal audio equipment for audio entertainment, and users of such personal audio equipment are consciously exposing themselves to loud volumes while situating in a noisy environment, which poses a threat to noise-induced hearing loss.

There are two types of noise reduction earphones, which are generally categorized in terms of how they are worn by the user. These two types are referred to as around-the-ear earpieces and in-the-ear earpieces. Usually, a conventional around-the-ear earpiece is a bulky device that uses sponges as its acoustic damping materials, and resembles an earmuff that covers and surrounds ears of a user for passive noise attenuation. However, it is not easy to carry because of its large size. With regard to those conventional in-the-ear earpieces, they are designed to fit into ear canal so that they can be fixedly stuffed inside the ears for blocking out external noises. Unlike the around-the-ear earpieces, the in-the-ear earpieces are easy to carry as they are light and compact. However, although the in-the-ear earpiece can provide better acoustic isolation effect, it may cause ear discomfort since it can seal the ear canal completely and therefore cause imbalance in air pressure. In addition, it is sensitive to the so-called internal noises. That is, when a user having a conventional in-the-ear earpiece fitted inside his/her ears, the sounds of speaking, swallowing, muscle/joints movements, etc., are seemingly to be amplified and thus clearly audible to the user.

An improved headphone with active circuit design for noise filtering was provided in U.S. Pat. No. 4,455,675, entitled "Headphoning". In U.S. Pat. No. 4,455,675, an acoustic control system is provided, which uses acoustic waves generated by acoustical sensing means for compensating and thus eliminating unwanted acoustic waves. The abovementioned technique had been vastly applied in related industries. Nevertheless, it can only be used for canceling out noises of low-frequency range, such as those of several kHz, but cannot be used for canceling out noises of high-frequency range since it cannot synchronize with the phases of those high-frequency noises. Therefore, the earmuff-like structure is still required for blocking out the high-frequency noises. There are many other noise reduction devices being successively disclosed thereafter, such as the one disclosed in U.S. Pat. No. 4,985,925, entitled "Active Noise Reduction System", which may use electronic parts or circuit layouts different from those shown in U.S. Pat. No. 4,455,675. However, the primary design of using an active circuit for noise attenuation remains the same and thus they all fail in high-frequency noise cancellation.

FIG. 1 shows an in-the-ear headphone disclosed in U.S. Pat. No. 6,683,965, entitled "In-the-ear Noise Reduction Headphones". The aforesaid in-the-ear headphone includes a shell 14 that has an extended portion 16 being shaped and sized to fit into the concha of a user's ear. In addition, an internal cavity 28 is defined in the shell 14 that is channeled with a passageway 29 extending through the extended portion 16. A speaker 32 is arranged inside the passageway 29 while arranging a microphone 34 in the passageway 29 at a position beneath the speaker 32. By the arrangement of the speaker 32, the microphone 34, and the acoustic connection between the passageway 29 and the ear canal, noise reduction can be achieved. However, as the cavity 28 and the passageway 29 are not structured to equip with filtering ability, noise of high-frequency range cannot be filtered thereby.

FIG. 2 shows a feedback type active noise control earphone, disclosed in TW Pat. No. 91213715. The feedback type active noise control earphone is primarily structured as a housing 140 having at least a speaker 110 arranged thereon, in which at least a microphone sensors 120 is installed around each speaker 110 for sensing ambient noise and thus converting the sensed noise into a noise signal to be received by the active noise control circuit 130 for enabling the same to generate a noise reduction signal. Therefore, each speaker 110 is enabled to produce an inverse phase audio signal with respect to the noise reduction signal. As each microphone sensor 120 is positioned in front of its corresponding speaker 110 while being arranged inside an energy vortex 150 generated inside the housing 140 by near-field effect, low frequency noise not only can be blocked from being received, but also can be cancelled by the inverse phase audio signal of the speaker 110. Nevertheless, the aforesaid earphone can only attenuate low frequency noise. In addition, not only the positioning of the microphone sensor is restricted to be placed in front of the speaker, but also the cooperation of the housing 140 and the active noise control circuit 130 is required.

FIG. 3 shows a headphone apparatus 10 with feedback type noise cancellation facility disclosed in U.S. Pat. No. 5,668,883, entitled "Headphone Apparatus Including An Equalizer System Having An Open Loop Characteristic With A Rising Slope Outside The Cancellation Band". The headphone apparatus 10 of FIG. 3 includes an acoustic pipe 6, a loudspeaker unit 5, a microphone unit 9 and a feedback circuit. The acoustic pipe 6 has an inner diameter W substantially equal to that $W_0$ of an external auditory canal A. The acoustic pipe 6 has a mounting portion provided at an end thereof for being mounted on the outer ear and has an acoustically non-reflective end at the other end thereof. With the aforesaid headphone apparatus, since the open loop characteristic of the equalizing section 3 by way of which the output signal of the microphone unit 9 provided on the acoustic pipe 6 having an inner diameter W substantially equal to that $W_0$ of the external auditory canal A is fed back to the loudspeaker unit 5 also provided on the acoustic pipe 6 is set to the characteristic, wherein the attenuation characteristic outside the frequency band in which noise can be canceled rises higher than the attenuation characteristic in the frequency characteristic in which noise can be canceled, the noise attenuation amount can be increased and the frequency band in which noise can be canceled can be widened. In other words, the headphone apparatus 10 of FIG. 3 includes amplifier set-up so that the gain characteristic outside cancellation band corresponds to the open loop characteristic. The output of the microphone unit 9 is fed back to the signal input system to the loudspeaker unit 5, thereby constructing a noise cancellation circuit of the feedback type. Noise Pin admitted into the inside of the acoustic pipe 6 of the headphone apparatus 10 from the outside is examined here. A sound pressure Po acting upon the ear-drum B is given, from the character of feedback, and the noise Pin arrives at the ear-drum B after it is attenuated by an amount corresponding to the loop gain.

FIG. 4 shows an earplug for selective filtering of sound transmission into the external auditory canal, disclosed in U.S. Pat. No. 5,832,094, entitled "Device Of Transmission Of Sound With Selective Filtering For Insertion In The Outer Auditory Canal". The sound transmission device with selective filtration for being placed in the external auditory canal of a user, as shown in of FIG. 4, includes a plug 1 provided with a hole 2 and an acoustic valve 8 at least partially within said plug 1. Said plug 1 is fittable in the auditory canal of the user. The device comprises a tube 3 which opens at its inner end into the residual cavity 7 existing between the plug 1 and the eardrum 4, and opening at its outer end into the acoustic valve 8. The acoustic valve 8 defines at one resonance cavity 10, 11, wherein said residual cavity 7 and said acoustic valve 8 are acoustically coupled by said tube 3 so as to form a fourth-order acoustic filter. Furthermore, the tube 3 extends through the plug 1 and opens into a space defined by the plug 1 and the eardrum 4 of a user. The opposite end of the tube 3 is connected to an acoustic valve 8 which is partially or wholly inserted in the plug 1 and contains one or more resonance cavities 10, 11. This invention is to provide a sound transmission device with selective filtering in the form of a plug that completely blocks the outer auditory canal. The plug includes an acoustic valve and an open tube associated with at least one resonance cavity of the valve. According to the well known HELMHOLTZ resonator principle, the acoustic filter thus obtained is a fourth order filter with an attenuation slope of 30 decibels per octave.

SUMMARY OF THE INVENTION

The present invention provides a noise reduction device with at lease one of noise reduction circuit and filtering cavity structure design, by which the reduction of audio high-frequency range noises can be achieved by at least an operation of a low-pass filter formed by the cavity structure, and the reduction of audio low-frequency noise range can be achieved by the operation of the noise reduction circuit, so that audio full frequency range noise reduction can be achieved as well.

The present invention also provides a noise reduction device that improves the ear discomfort of imbalance in air pressure, caused by the sealing of the ear canal completely for noise reduction.

The present invention provides a noise reduction device, comprising:

a cavity;

a plurality of ducts, each of the ducts being connected to the cavity for transmitting an acoustic signal including a noise signal into/out of the cavity;

a noise reduction circuit, for receiving the acoustic signal including the noise signal and generating an electrical signal;

a microphone for receiving the acoustic signal inside the cavity, converting the received acoustic signal into another electrical signal and transmitting the electrical signal to the noise reduction circuit; and a speaker for receiving the electrical signal generated by the noise reduction circuit, using the received electrical signal to generate an out of phase acoustic signal accordingly, and feeding the out of phase acoustic signal into the cavity to interfere with the noise signal inside the cavity, thereby reducing the noise signal inside the cavity.

The present invention provides a noise reduction method, comprising the steps of:

(a) providing an outer duct for transmitting an acoustic signal (including a noise signal) into a cavity;

(b) using a microphone to received the noise signal from the cavity while converting the received noise signal into an electrical signal;

(c) using a noise reduction circuit to receive the electrical signal generated by the microphone while enabling a speaker to generate an out of phase acoustic signal to interfere with the noise signal inside the cavity so as to cancel out the noise signal inside the cavity; and (d) using an inner duct to transmit the acoustic signal, being filtered out of noises, out of the cavity.

With the aforesaid device and method, not only audio high-frequency range noises can be reduced by an operation of a low-pass filter formed by the combined structure of the cavity and the ducts, but also audio low-frequency noise range is reduced by the noise reduction circuit as it can direct the speaker to generate an out of phase acoustic signal for canceling out the audio low-frequency range noise, so that audio full frequency range noise reduction can be achieved.

Further scope of applicability of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention and wherein.

DESCRIPTION OF THE EXEMPLARY EMBODIMENTS

Figure 5:
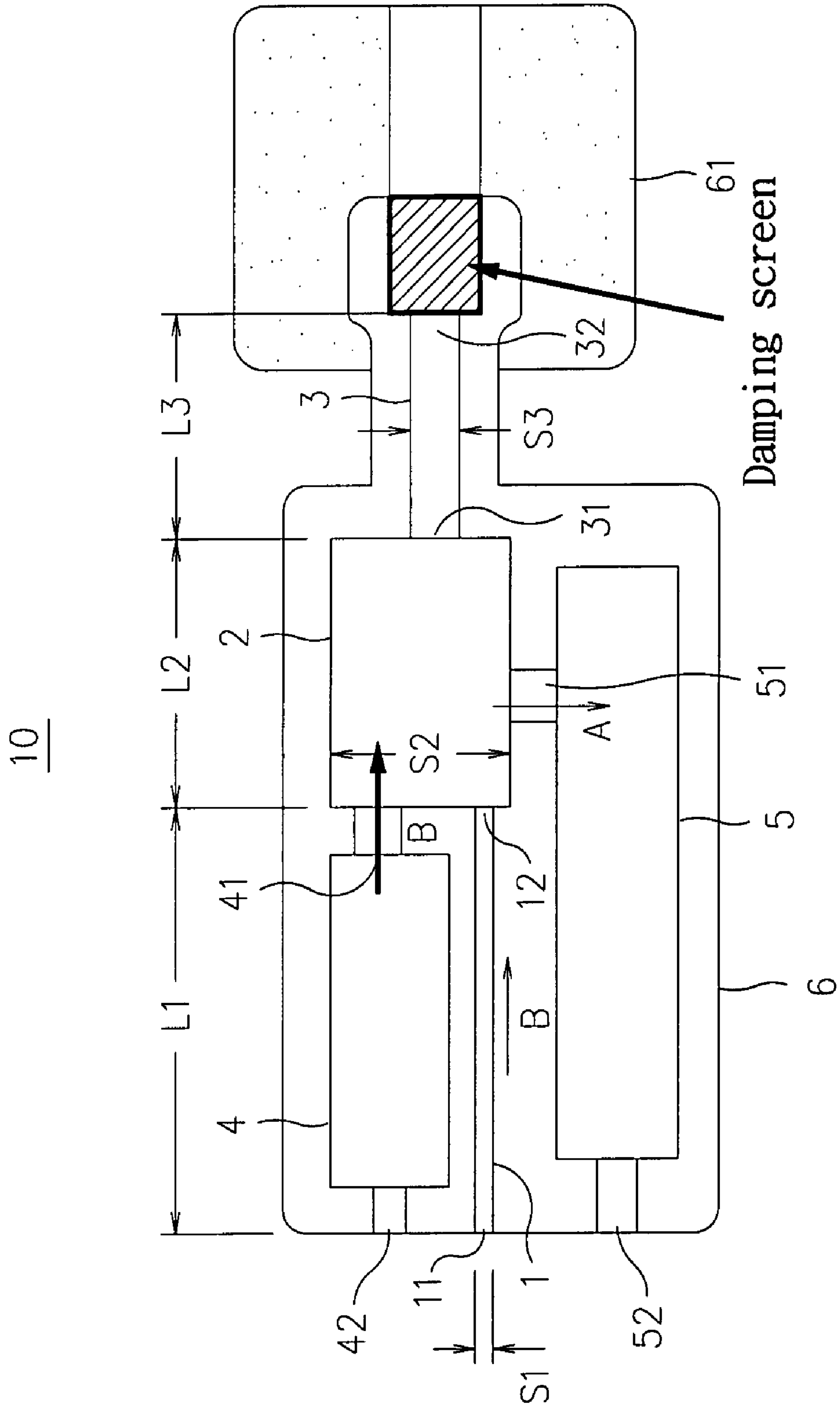
FIG. 5 is a schematic diagram showing a noise reduction device of an embodiment of the invention.
Figure 6:
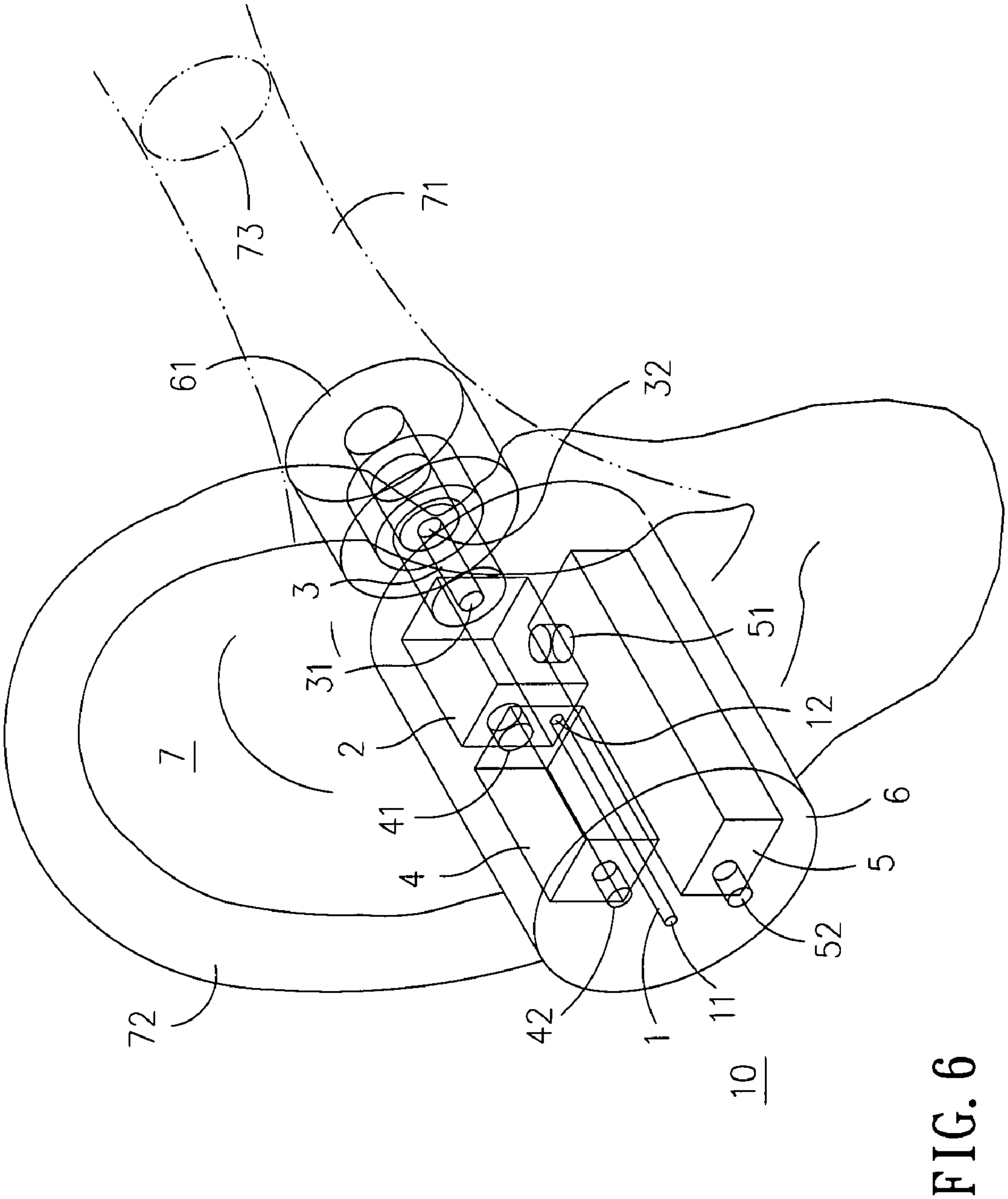
FIG. 6 shows a noise reduction device of an embodiment of the invention, being applied to a human ear.

The noise reduction device in an exemplary embodiment of the present invention can be divided into two parts, one of which is an acoustic wave filter and the other is a noise reduction circuit. The structure of the acoustic wave filter is shown in FIG. 5 and FIG. 6. The noise reduction device 10 includes a housing 6 with a cavity 2 defined therein, in which the cross-sectional area of the cavity 2 is represented as S2 and its length is represented as L2. An outer duct 1 is arranged at an end of the cavity 2 while arranging an inner duct 3 at another end of the cavity 2. The outer duct 1 has an input end 11 and an output end 12. The input end 11 extends through the housing 6 and is channeled with ambient environment of the housing 6, and the output end 12 is connected and channeled with the cavity 2. The cross-sectional area of the outer duct 1 is represented as S1 and its length is represented as L1. The inner duct 3 has an input end 31 and an output end 32. The input end 31 is connected and channeled with the cavity 2, and the output end 32 extends through the housing 6 and is channeled with a human ear canal 71. The cross-sectional area of the inner duct 3 is represented as S3 and its length is represented as L3. As the outer duct 1 and the inner duct 3 extend through the whole cavity 2, the cavity 2 is channeled with the ambient environment of the housing 6. In addition, a plug structure 61 and a damping screen 62 are formed at a position of the housing 6 corresponding to the output end 32 of the inner duct 3 that is structured to fit into an ear canal 71 of a human ear 7 and thus prevent noise from entering the human ear canal 71. The portion of the housing excluding the plug structure 61 is made of soft rubber, plastic or sponge, and can be mounted on the auricle 72 of the ear 7. There is no specific requirement or limitation for the size, shape and material of the plug structure 61, as long as it can perfectly and comfortably match with the ear canal 71. It is noted that the matching of the plug structure 61 and the housing 6 may vary with respect to the actual size of the housing 6 as well as the shape and material of the plug structure 61. As the cavity 2 is connected to the ear canal 71 and the ambient environment respectively by the inner and the outer ducts 1, 3, the cavity 2 can be used for balancing inner and outer ear pressure while subject to static pressure and is equipped with high-frequency noise attenuation ability while subject to dynamic pressure.

Moreover, a microphone 5 is arranged inside the housing 6, which is usually a mini-microphone. An aperture 51 is formed at a position between the microphone 5 and the cavity 2 for enabling the microphone 5 to receive and measure acoustic signals inside the cavity 2. The size of the aperture 51 depends upon the type of the microphone 5. A connector 52 is provided on the housing 6 at a position corresponding to the microphone 5 for connecting the microphone 5 to an external circuit in a wired manner. It is noted that the reception direction A of the microphone 5 to the acoustic signal through the aperture 51 is perpendicular to the direction B of the acoustic signal being transmitted into the cavity 5 from the outer duct 1.

In addition, a loudspeaker 4 is also arranged inside the housing 6, which is usually a speaker. An aperture 41 is formed at a position between the speaker 4 and the cavity 2 for enabling the speaker 4 to transmit acoustic signals into the cavity 2 therefrom. The size of the aperture 41 depends upon the type of the speaker. A connector 42 is provided on the housing 6 at a position corresponding to the speaker 4 for connecting the speaker 4 to an external circuit in a wired manner. It is noted that the connection of the microphone 5 to the external circuit as well as the speaker 4 thereto can be achieved by a wireless manner as long as it is suitable with respect to the structure space and size.

The housing 6 can be made of various materials, most commonly made of plastic, in which the outer duct 1, the cavity 2 and the inner duct 3 are all integrally formed therewith. The sizes of the outer duct 1, the cavity 2 and the inner duct 3 should be designed to match with each other while the cross-section area S2 of the cavity 2 is larger than the cross-section areas S1, S3 of the outer and inner ducts 1, 3. The cross sections of the outer duct 1, the cavity 2 and the inner duct 3 can be of any regular or irregular shape, but preferably to be circular. Moreover, the lengths L1, L2 and L3 of the outer duct 1, the cavity 2 and the inner duct 3 can be designed to be different from each other while the outer and the inner duct 1, 3 can be any regular or irregular curved shape. In addition, in order to prevent the acoustic signal from being reflected inside the cavity 2, the interior of the cavity 2 where it is connected to the inner and outer ducts 1, 3 are chamfered, or any two opposite inner walls of the cavity 2 are designed to be unparallel to each other, or a sound absorbing materials (such as sponge) is arranged on inner wall of the cavity 2.

By designing the outer duct 1, the cavity 2 and the inner duct 3 with various volumes and diameters, a low-pass filter can be formed by the combined structure of the cavity 2 and the two ducts 1, 3 that can allow only low-frequency acoustic wave to pass through. The number of ducts can be increased with respect to actual requirement so as to enhance the acoustic wave filtering ability of the low-pass filter. In this exemplary embodiment, only one outer duct 1 and one inner duct 3 are used. However, it is only for illustration and thus the present invention is not limited thereby. When the noise ambient to the housing 6 enters the cavity 2 through the input end 11 of the outer duct 1 and then exits from the cavity 2 through the inner duct 3, the noise in the audio high-frequency range will be filtered out by a low-pass filter formed by the combined structure of the cavity 2 and the two ducts 1, 3. It is noted that the referring audio high-frequency range is defined as the range between 1 KHz to 20 KHz, which is the limit of human audible range. With regard to the audio low-frequency range noise, being defined as the range under I KHz or several KHz, it can be reduced by the following process: as soon as the noise is received by the microphone 5, it is converted into a corresponding electrical signal by a feedback circuit while enabling the noise reduction circuit to generate an out of phase acoustic signal for directing the speaker 4 to produce an inverted acoustic wave. The inverted acoustic wave is transmitted to the cavity 2 for enabling the same to interfere with the audio low-frequency range of the noise signal and thus cancel out each other. In other words, by the operation of the aforesaid audio low-pass filter and the noise reduction circuit, not only noises in the audio high-frequency range can be reduced, but also noises in the audio low-frequency range is reduced. Therefore, full audio frequency range noise reduction can be achieved. While applying aforesaid device in an earphone, the acoustic signal intended to be received by the earphone will not be affected since the inverted noise-reduction signal is superposed upon the original intended acoustic signal that is only going to interfere with the noise portion of the acoustic signal. In addition, as the acoustic wave emitted from the speaker 4 will not be transmitted through the passageway of the outer duct 1, the cavity 2 and the inner duct 3, it will not be affected by the low-pass filter formed by the combined structure of the cavity 2 and the two ducts 1, 3.

The microphone 5 can receive the noise signal so as to use the received noise signal for enabling the convergence of acoustic wave interference. It can prevent the whole noise reduction device from being a noise generator by resonance. Therefore, the microphone should be positioned in front of the speaker 4, i.e., at a position between the speaker 4 and an ear canal 71. Noises can be measured by the microphone 5, and thus can be completely canceled by the inverted noise-reduction signal of the speaker 4 inside the cavity 2 to protect the eardrum 73. The aforesaid process can be referred to as the closed loop feedback control method. With regard to the arrangement of the speaker 4 and microphone 5 in a conventional noise reduction system, the microphone 5 is placed at a position behind the speaker 4. Therefore, not only the convergence of acoustic wave interference cannot be ensured, but also it is possible to cause damage to eardrum 73 while there is malfunction in the feedback circuit since the inverted noise-reduction signal is not superposed upon the original intended acoustic signal.

Figure 7:
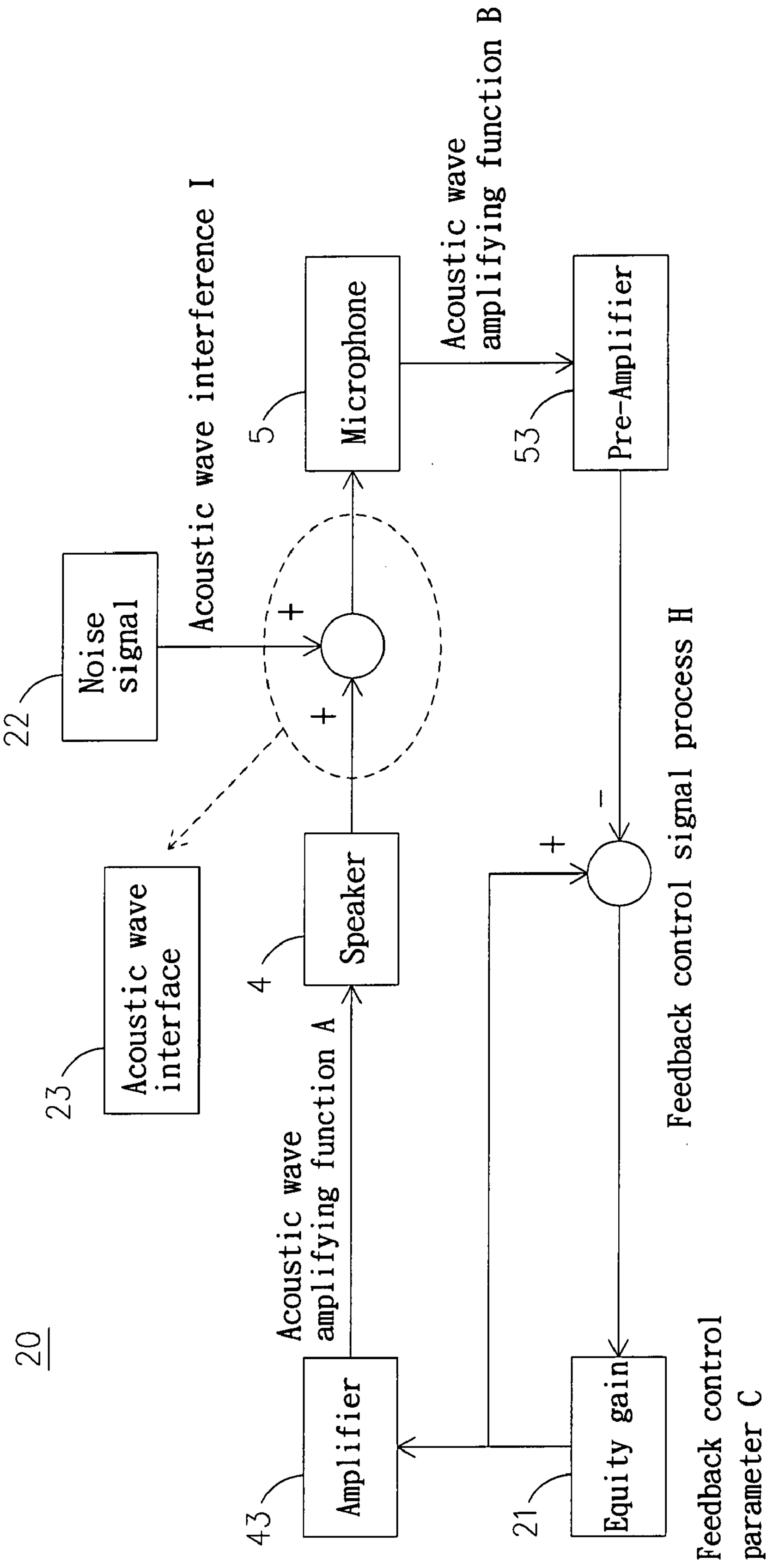
FIG. 7 shows an active noise reduction schematic used in a noise reduction device of an embodiment of the invention.

The noise reduction circuit used in the noise reduction device 10 in the exemplary embodiment is primary for reducing low-frequency noise. It is intended to briefly outline the design concept of the control circuit in the exemplary embodiment as well as the corresponding noise reduction control process 20, as seen in FIG. 7, in which parameters are defined as follows:

(1) the speaker 4 and the power amplifier 43, parameter being defined as acoustic wave amplifying function A;

(2) the microphone 5 and the pre amplifier 53, parameter being defined as acoustic wave amplifying function (3) feedback control parameter C of the gain loop 21;

(4) acoustic wave interference I of the noise signal 22, which refers to the canceling out of the acoustic signal in the cavity 2 with the inverted acoustic signal generated by the speaker 4;

(5) feedback control signal process H, being used for synthesizing and comparing the acoustic signal being processed by the pre amplifier 53 and the gain loop 21 for adjusting the same.

Figure 8:
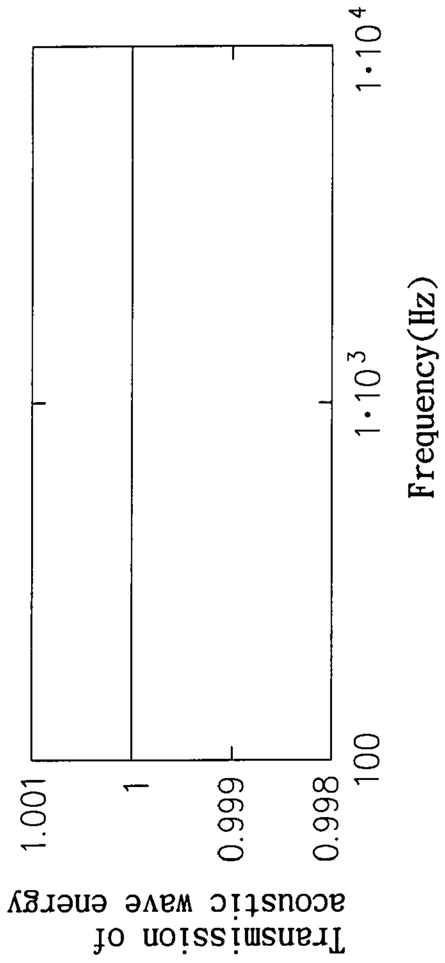
FIG. 8 shows the transmission of acoustic wave energy with respect to noise frequency as the cross-sectional areas of the outer duct, the cavity and the inner duct of the invention are designed to be the same.

In FIG. 8, the acoustic wave interface 23 represents the combined stricture of the cavity 2 and the two ducts 1,3. Assuming noise is represented as P(n) and the signal generated by the speaker 4 is represented as P(v), as the transmission speed of the acoustic wave is far slower than the electrical signal, the time sequence of the noise signals can be represented as (P(n), P(n+1), P(n+2), . . . ) and thus its logic control can be exemplary as follows:

$$P(v) = -ABC\cdot P(n) \quad (1)$$

$$P(i) = P(v) + P(n+1) = P(n+1) - ABC\cdot P(n)$$

$$P(v+1) = \mathrm{AC}(-ABC\cdot P(n) - B\cdot P(i))$$

$$= \mathrm{AC}(-BC\cdot P(n) + AB^2C\cdot P(n) - B\cdot P(n+1))$$

When $AB = 1$ $$P(v+1) = -ABC\cdot P(n+1)$$

As illustrated in Function (1), the convergence of acoustic wave interference can be achieved by the noise feedback control circuit in the exemplary embodiment of the present invention that the instability caused by time difference between acoustic wave and electrical signal will not occur. The aforesaid logic control is used primarily for solving the time difference caused by the relative positioning distance of the speaker 4 and the microphone 4. As the noise signal 22 is composed of acoustic wave of different frequencies, each of signal-frequency acoustic wave is explored by representing the signal-frequency acoustic wave as P1 while representing its inverted acoustic signal as P2, the time difference between P1 and P2 will be dt=dL/v, whereas dL is the relative positioning distance of the speaker 4 and the microphone 4, and v is the speed of acoustic wave, and dP is signal relating to the acoustic interference, by which:

$$P1=\sin(w\cdot t+dt)$$

$$P2=\sin(w\cdot t+\pi)$$

$$Dt=dL/v$$

$$DP=P1+P2 \quad (2)$$

As illustrated in Function (2), the time difference caused by the relative positioning distance of the speaker 4 and the microphone 4 will affect the magnitude of the acoustic amplitude after being interfered while the frequency w will not affect the interference. That is, the anti-noise logic control will not be affected by the variation of frequency, and the parameter relating to frequency can be ignored.

Figure 1:
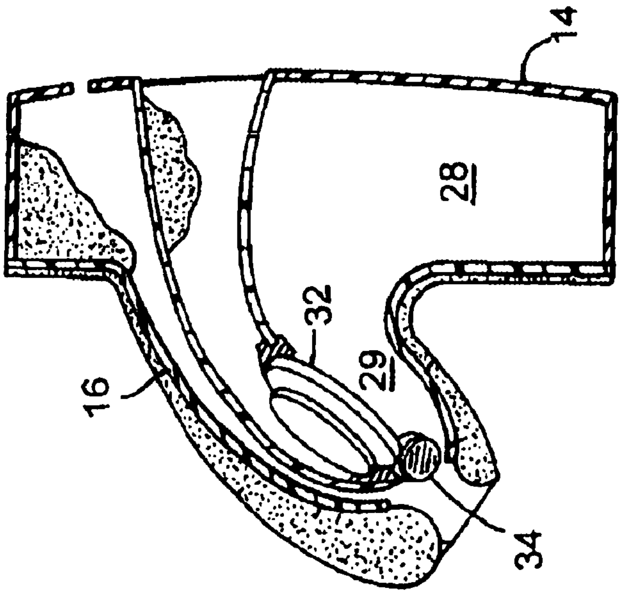
FIG.1 (PRIOR ART)
FIG. 1 is a schematic diagram showing an in-the-ear headphone, disclosed in U.S. Pat. No. 6,683,965, entitled "In-the-ear Noise Reduction Headphones".
Figure 2:
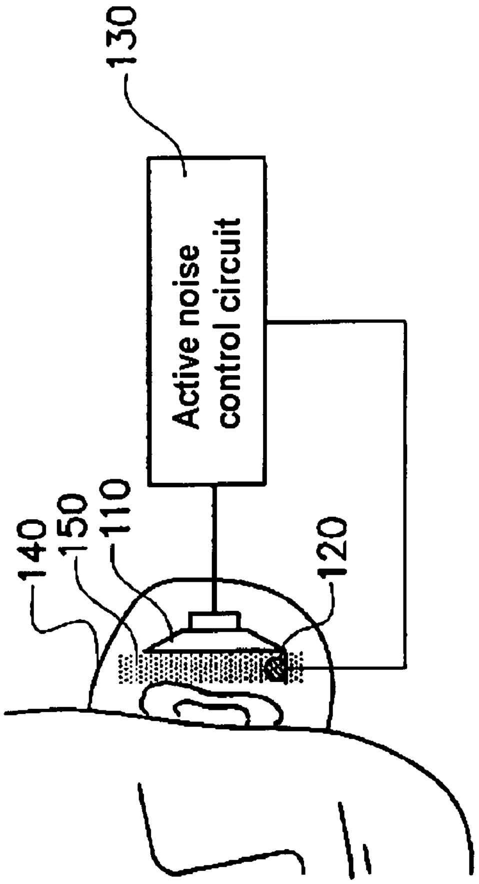
FIG.2 (PRIOR ART)
FIG. 2 is a schematic diagram showing a feedback type active noise control earphone, disclosed in TW Pat. No. 91213715.
Figure 4:
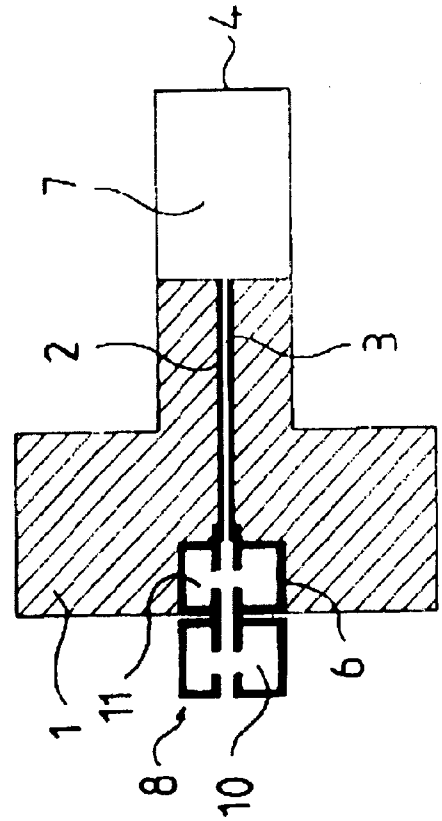
FIG.4 (PRIOR ART)
FIG. 4 is a schematic diagram showing an earplug for selective filtering of sound transmission into the external auditory canal, disclose in U.S. Pat. No. 5,832,094.
Figure 3:
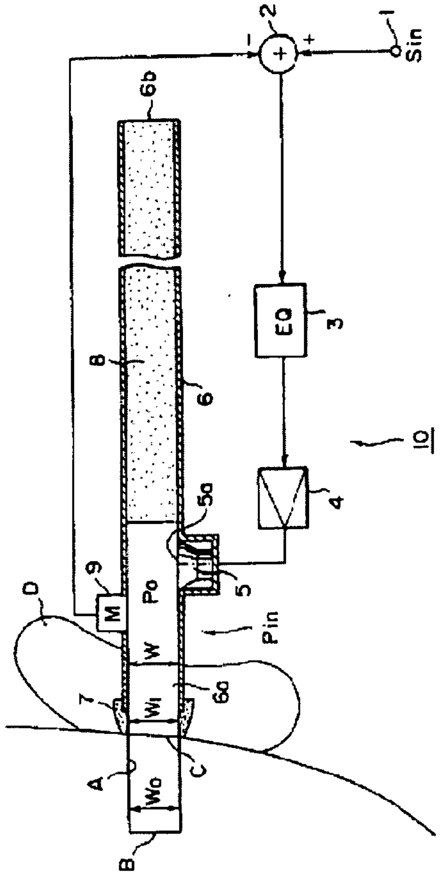
FIG.3 (PRIOR ART)
FIG. 3 is a schematic diagram showing a headphone apparatus including an acoustic pipe, disclosed in U.S. Pat. No. 5,668,883.

From the above description, the filter structure composed of the outer duct 1, the cavity 2, the inner duct 2 is able to reduce the audio high-frequency range noises that cannot be reduced by the traditional noise cancel circuit. With regard to the audio low-frequency range noises, it can be reduced by the noise reduction circuit. In the exemplary embodiment as shown in FIG. 3, the cross-section area of the outer duct 1 is smaller than 100 $mm^2$ while its length can be smaller than 30 mm, the volume of the cavity 2 can be smaller than 5 $cm^2$ while its length can be smaller than 20 mm, and the cross-section area of the inner duct 3 can be smaller than 100 $mm^2$ while its length can be smaller than 30 mm.

Figure 9:
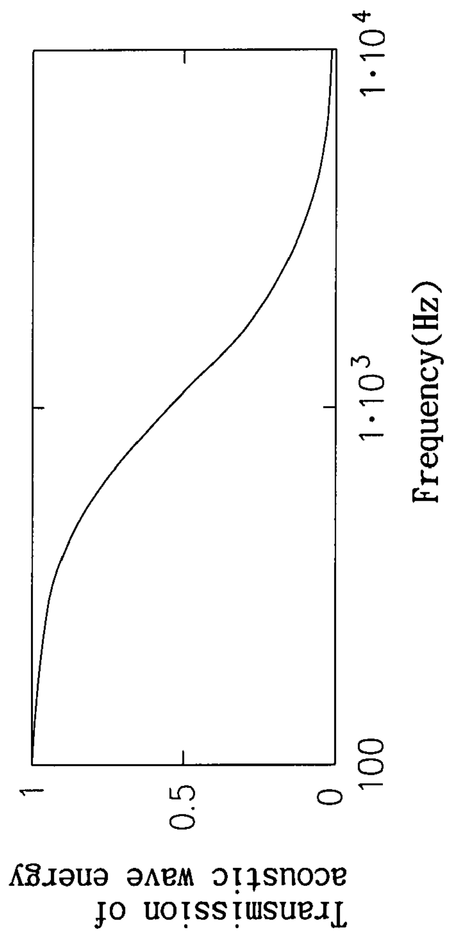
FIG. 9 shows the transmission of acoustic wave energy with respect to noise frequency as the cross-sectional areas of the outer duct, the cavity and the inner duct of the invention are designed to not be the same.

When S1=S2=S3, the transmission of acoustic wave energy after passing the cavity 2 is not reduced as shown in the frequency spectrum of FIG. 8. When S1=S3=3.142 $mm^2$ and S2=314.2 $mm^2$, the transmission of acoustic wave energy relating to high-frequency range is reduced as shown in the frequency spectrum of FIG. 9. By which, it is known that the cross-sectional area of the cavity S2 should be larger than the cross-sectional areas S1, S3 of the outer and inner ducts 1, 3.

Figure 10:
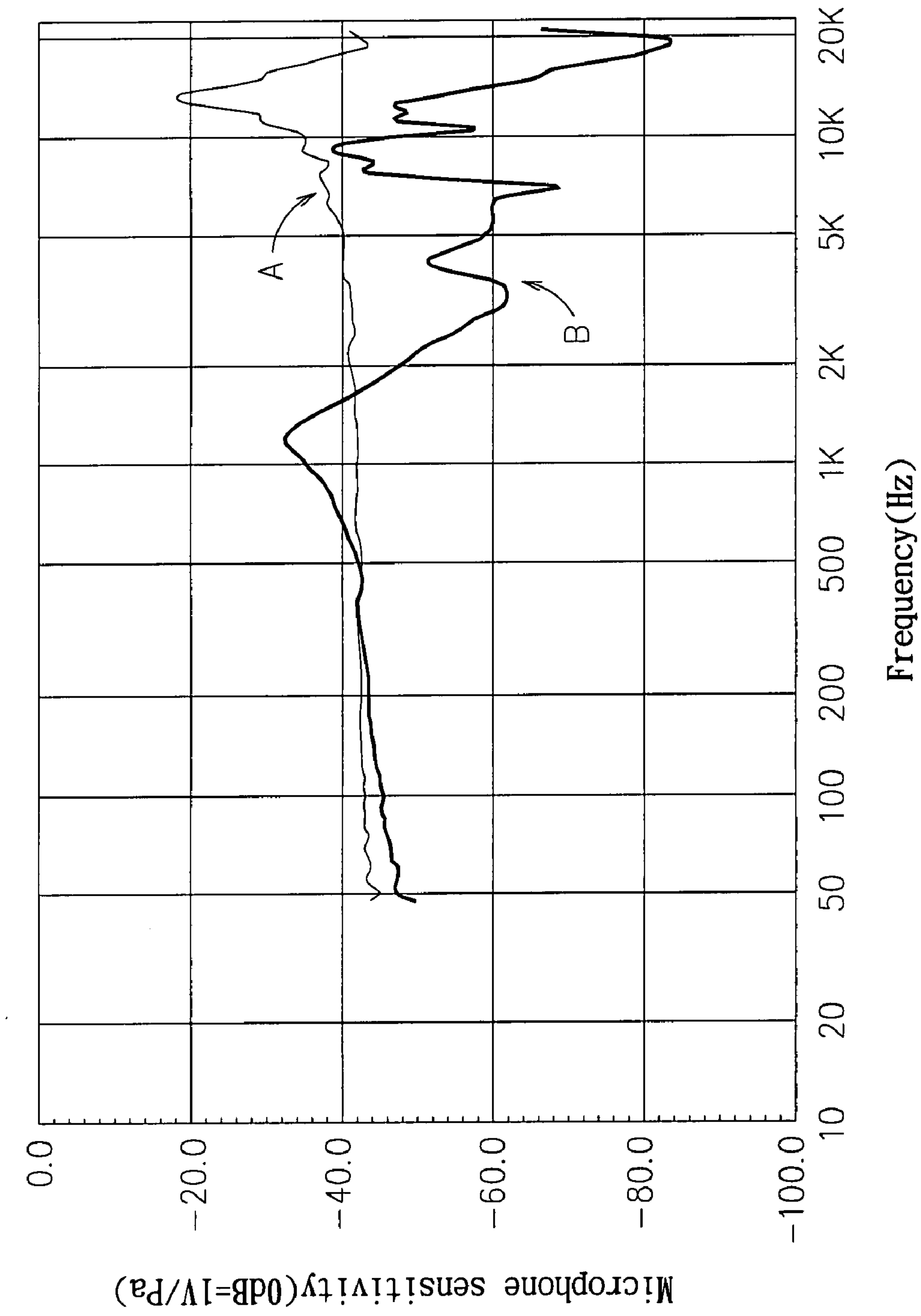
FIG. 10 shows the comparison of two noise characteristic curves, depicting that the audio high-frequency noise range is reduced by the noise reduction device of an embodiment of the invention.

FIG. 10 shows the comparison of two noise characteristic curves, depicting that the audio high-frequency noise range can be reduced by the noise reduction device of the invention. The curve A is the ambient noise signal measured by the microphone 5, and the curve B is the acoustic signal measured inside the noise reduction device 10 of the invention. As shown in FIG. 10, the audio high-frequency range noises, referred to as those have frequencies higher than 2 KHz, can actually be canceled by interference.

From the above description, a noise reduction method comprises the steps of:

(a) providing an outer duct for transmitting an acoustic signal (including a noise signal) into a cavity;

(b) using a microphone to received the noise signal from the cavity while converting the received noise signal into an electrical signal;

(c) using a noise reduction circuit to receive the electrical signal generated by the microphone while enabling a speaker to generate an out of phase acoustic signal to interfere with the noise signal inside the cavity so as to cancel out the noise signal inside the cavity; and (d) using an inner duct to transmit the acoustic signal, being filtered out of noises, out of the cavity.

To sum up, the present invention can provide a noise reduction device with noise reduction circuit and cavity structure design for achieving not only the reduction of audio high-frequency range noises by an operation of a low-pass filter formed by the cavity structure, but also the reduction of audio low-frequency noise range by the noise reduction circuit, so that audio full frequency range noise reduction is achieved.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A noise reduction device, comprising:

a housing comprising an acoustic wave filter comprising a cavity formed by a plurality of sidewalls, and a plurality of ducts having at least one outer duct and at least one inner duct, each of the ducts being connected to the sidewall of the cavity for transmitting an acoustic signal including a noise signal into/out of the cavity;

a speaker connected to the cavity; and a microphone arranged between the speaker and a human ear canal, and configured to simultaneously channel with the cavity and the at least one outer duct;

a noise reduction circuit configured to receive the acoustic signal including the noise signal and generating an electrical signal; and a plug connected to the housing through the at least one inner duct, and configured to be tightly fitted inside the human ear canal and to prevent noise from entering the human ear canal, wherein the microphone is configured to receive the acoustic signal inside the cavity, convert the received acoustic signal into another electrical signal and transmit the electrical signal to the noise reduction circuit;

wherein the speaker is configured to receive the electrical signal generated by the noise reduction circuit, use the received electrical signal to generate an out of phase acoustic signal accordingly, and feed the out of phase acoustic signal into the cavity to interfere with the noise signal inside the cavity, so as to reduce the noise signal inside the cavity, and wherein the acoustic wave filter is configured to reduce high-frequency range noises while the noise reduction circuit is configured to reduce low-frequency range noises.

2. The noise reduction device of claim 1, wherein the cross-sectional area of the cavity is larger than that of each one of the ducts.

3. The noise reduction device of claim 1, wherein the length of the cavity is unequal to that of each one of the ducts.

4. The noise reduction device of claim 1, wherein the at least one outer duct is configured to be a passageway provided for the acoustic signal to be transmitted into the cavity, and the at least one inner duct is configured to transmit a processed acoustic signal out of the cavity, wherein the processed acoustic signal is the acoustic signal being filtered out of the audio high-frequency range noises.

5. The noise reduction device of claim 4, wherein the length and the cross-sectional area of the outer duct are not the same as those of the inner duct.

6. The noise reduction device of claim 1, wherein the microphone is connected to a feedback circuit for inverting the acoustic signal to be received by the speaker.

7. The noise reduction device of claim 1, wherein the cavity, the ducts, and the housing are integrally formed.

8. The noise reduction device of claim 1, wherein the housing includes a connector, provided for connecting the microphone to an external circuit in a wired manner.

9. The noise reduction device of claim 1, wherein the housing includes a connector, provided for connecting the speaker to an external circuit in a wired manner.

10. The noise reduction device of claim 1, wherein any one of the microphone and the speaker is connectable to an external circuit in a manner selected from the group consisting of a wired manner and a wireless manner.

11. The noise reduction device of claim 1, wherein an aperture is formed at a position between the microphone and the cavity for enabling the microphone to receive the acoustic signal therefrom, and the reception direction of the microphone to the acoustic signal through the aperture is perpendicular to the direction of the acoustic signal being transmitted into the cavity from the plural ducts.

12. The noise reduction device of claim 1, wherein the interior of the cavity where it is connected to each of the ducts is chamfered.

13. The noise reduction device of claim 1, wherein a sound absorbing material is arranged on inner wall of the cavity.

14. The noise reduction device of claim 1, wherein any two opposite sidewalls of the cavity are unparallel to each other.

15. The noise reduction device of claim 1, wherein the shape of the cavities is selected from the group consisting of a regular shape and an irregular shape.

16. The noise reduction device of claim 1, wherein the shape of each of the plurality of ducts is selected from the group consisting of a regular shape and an irregular shape.

17. A noise reduction method, comprising the steps of:

forming an acoustic wave filter by connecting a plurality of ducts having at least one outer duct and at least one inner duct to a cavity formed by a plurality of sidewalls, and;

transmitting an acoustic signal including a noise signal through the at least one outer duct into the cavity;

receiving the noise signal by a microphone from the cavity while converting the received noise signal into an electrical signal;

using a noise reduction circuit to receive the electrical signal generated by the microphone while enabling a speaker to generate an out of phase acoustic signal, to interfere with the noise signal inside the cavity so as to reduce the noise signal inside the cavity; and transmitting the acoustic signal, being filtered out of noises, out of the cavity to a plug through the at least one inner duct, wherein the microphone is arranged between the speaker and a human ear canal, and configured to simultaneously channel with the cavity and the at least one outer duct, and wherein the plug is configured to be tightly fitted inside the human ear canal and to prevent noise from entering the human ear canal.

18. The noise reduction method of claim 17, wherein audio high-frequency range noises of the acoustic signal are filtered while the acoustic signal enters the cavity as the cross-sectional area of the cavity is larger than both cross-sectional areas of the inner and outer ducts.

19. The noise reduction method of claim 17, wherein the length and the cross-sectional area of the outer duct are not the same as those of the inner duct.

20. The noise reduction method of claim 17, wherein the noise reduction circuit further comprises a feedback circuit transmitting the electrical signal to the speaker so as to generate the out of phase acoustic signal.

* * * * *